United States Patent
Beaver

(10) Patent No.: US 11,361,161 B2
(45) Date of Patent: Jun. 14, 2022

(54) AUTOMATED SYSTEM AND METHOD TO PRIORITIZE LANGUAGE MODEL AND ONTOLOGY EXPANSION AND PRUNING

(71) Applicant: Verint Americas Inc., Alpharetta, GA (US)

(72) Inventor: Ian Beaver, Spokane, WA (US)

(73) Assignee: Verint Americas Inc., Alpharetta, GA (US)

( * ) Notice: Subject to any disclaimer, the term of this patent is extended or adjusted under 35 U.S.C. 154(b) by 317 days.

(21) Appl. No.: 16/659,913

(22) Filed: Oct. 22, 2019

(65) Prior Publication Data

US 2020/0125798 A1    Apr. 23, 2020

Related U.S. Application Data

(60) Provisional application No. 62/748,636, filed on Oct. 22, 2018.

(51) Int. Cl.
*G06F 40/289*    (2020.01)
*G06N 20/00*    (2019.01)

(52) U.S. Cl.
CPC .......... *G06F 40/289* (2020.01); *G06N 20/00* (2019.01)

(58) Field of Classification Search
None
See application file for complete search history.

(56) References Cited

U.S. PATENT DOCUMENTS

| | | | |
|---|---|---|---|
| 5,317,673 A | 5/1994 | Cohen et al. | |
| 5,737,617 A | 4/1998 | Bernth et al. | |
| 6,076,088 A | 6/2000 | Paik et al. | |
| 6,434,557 B1 | 8/2002 | Egilsson et al. | |
| 6,560,590 B1 | 5/2003 | Shwe et al. | |
| 6,718,296 B1 | 4/2004 | Reynolds et al. | |
| 7,113,958 B1 | 9/2006 | Lantrip et al. | |
| 7,552,053 B2 | 6/2009 | Gao et al. | |
| 7,734,467 B2 | 6/2010 | Gao et al. | |
| 7,844,459 B2 | 11/2010 | Budde et al. | |
| 7,853,544 B2 | 12/2010 | Scott et al. | |
| 7,904,414 B2 | 3/2011 | Isaacs | |
| 7,912,701 B1 | 3/2011 | Gray et al. | |
| 8,036,876 B2 | 10/2011 | Sanfilippo et al. | |
| 8,078,565 B2 | 12/2011 | Arseneault et al. | |
| 8,160,232 B2 | 4/2012 | Isaacs et al. | |
| 8,190,628 B1 | 5/2012 | Yang et al. | |

(Continued)

FOREIGN PATENT DOCUMENTS

WO    WO-0026795 A1 *    5/2000    ............. G06F 40/30

OTHER PUBLICATIONS

Search Report, dated Mar. 3, 2020, received in connection with corresponding EP Patent Application No. 19204698.5.

(Continued)

*Primary Examiner* — Quynh H Nguyen

(74) *Attorney, Agent, or Firm* — Meunier Carlin & Curfman LLC

(57) ABSTRACT

A system and method for updating computerized language models is provided that automatically adds or deletes terms from the language model to capture trending events or products, while maximizing computer efficiencies by deleting terms that are no longer trending and use of knowledge bases, machine learning model training and evaluation corpora, analysis tools and databases.

19 Claims, 2 Drawing Sheets

(56) References Cited

U.S. PATENT DOCUMENTS

| | | |
|---|---|---|
| 8,260,809 B2 | 9/2012 | Platt et al. |
| 8,285,552 B2 | 10/2012 | Wang et al. |
| 8,447,604 B1 | 5/2013 | Chang |
| 8,825,488 B2 | 9/2014 | Scoggins et al. |
| 8,825,489 B2 | 9/2014 | Scoggins et al. |
| 8,874,432 B2 | 10/2014 | Qi et al. |
| 9,066,049 B2 | 6/2015 | Scoggins et al. |
| 9,189,525 B2 | 11/2015 | Acharya et al. |
| 9,232,063 B2 | 1/2016 | Romano et al. |
| 9,355,354 B2 | 5/2016 | Isaacs et al. |
| 9,477,752 B1 | 10/2016 | Romano |
| 9,569,743 B2 | 2/2017 | Fehr et al. |
| 9,575,936 B2 | 2/2017 | Romano et al. |
| 9,639,520 B2 | 5/2017 | Yishay |
| 9,646,605 B2 | 5/2017 | Biatov et al. |
| 9,697,246 B1 | 7/2017 | Romano et al. |
| 9,720,907 B2 | 8/2017 | Bangalore et al. |
| 9,760,546 B2 | 9/2017 | Galle |
| 2002/0032564 A1 | 3/2002 | Ehsani et al. |
| 2002/0128821 A1 | 9/2002 | Ehsani et al. |
| 2002/0188599 A1 | 12/2002 | McGreevy |
| 2003/0028512 A1 | 2/2003 | Stensmo |
| 2003/0126561 A1 | 7/2003 | Woehler et al. |
| 2004/0078190 A1 | 4/2004 | Fass et al. |
| 2004/0236737 A1 | 11/2004 | Weissman et al. |
| 2006/0248049 A1 | 11/2006 | Cao et al. |
| 2007/0016863 A1 | 1/2007 | Qu et al. |
| 2007/0118357 A1 | 5/2007 | Kasravi et al. |
| 2008/0021700 A1 | 1/2008 | Moitra et al. |
| 2008/0154578 A1 | 6/2008 | Xu et al. |
| 2009/0012842 A1 | 1/2009 | Srinivasan et al. |
| 2009/0043581 A1 | 2/2009 | Abbott et al. |
| 2009/0099996 A1 | 4/2009 | Stefik |
| 2009/0150139 A1 | 6/2009 | Jianfeng et al. |
| 2009/0204609 A1 | 8/2009 | Labrou et al. |
| 2009/0254877 A1 | 10/2009 | Kuriakose et al. |
| 2009/0306963 A1 | 12/2009 | Prompt et al. |
| 2009/0326947 A1 | 12/2009 | Arnold et al. |
| 2010/0030552 A1 | 2/2010 | Chen et al. |
| 2010/0057688 A1 | 3/2010 | Anovick et al. |
| 2010/0161604 A1 | 6/2010 | Mintz et al. |
| 2010/0275179 A1 | 10/2010 | Mengusoglu et al. |
| 2011/0161368 A1 | 6/2011 | Ishikawa et al. |
| 2011/0196670 A1 | 8/2011 | Dang et al. |
| 2012/0303356 A1 | 11/2012 | Boyle et al. |
| 2013/0018650 A1 | 1/2013 | Moore et al. |
| 2013/0066921 A1 | 3/2013 | Mark et al. |
| 2013/0132442 A1 | 5/2013 | Tsatsou et al. |
| 2013/0166303 A1 | 6/2013 | Chang et al. |
| 2013/0260358 A1 | 10/2013 | Lorge et al. |
| 2014/0040275 A1 | 2/2014 | Dang et al. |
| 2014/0075004 A1 | 3/2014 | Van Dusen et al. |
| 2014/0143157 A1 | 5/2014 | Jeffs et al. |
| 2014/0222419 A1 | 8/2014 | Romano et al. |
| 2014/0297266 A1 | 10/2014 | Nielson et al. |
| 2015/0066506 A1 | 3/2015 | Romano et al. |
| 2015/0074124 A1 | 3/2015 | Sexton et al. |
| 2015/0127652 A1 | 5/2015 | Romano |
| 2015/0169746 A1 | 6/2015 | Hatami-Hanza |
| 2015/0170040 A1 | 6/2015 | Berdugo et al. |
| 2015/0193532 A1 | 7/2015 | Romano |
| 2015/0220618 A1 | 8/2015 | Horesh et al. |
| 2015/0220626 A1 | 8/2015 | Carmi et al. |
| 2015/0220630 A1 | 8/2015 | Romano et al. |
| 2015/0220946 A1 | 8/2015 | Horesh et al. |
| 2016/0055848 A1 | 2/2016 | Meruva et al. |
| 2016/0078016 A1 | 3/2016 | Ng Tari et al. |
| 2016/0078860 A1 | 3/2016 | Paulik et al. |
| 2016/0180437 A1 | 6/2016 | Boston et al. |
| 2016/0217127 A1 | 7/2016 | Segal et al. |

OTHER PUBLICATIONS

Chen, S.F., et al., "An Empirical Study of Smoothing Techniques for Language Modeling," Computer Speech and Language, vol. 13, 1998, 62 pages.

Coursey, K., et al., "Topic identification using Wikipedia graph centrality," Proceedings of the 2009 Annual Conference of the North American Chapter of the Association for Computational Linguistics, Human Language Technologies, Short Papers, 2009, pp. 117-120.

Federico, M., et al., "IRSTLM: an Open Source Toolkit for Handling Large Scale Language Models," Ninth Annual Conference of the International Speech Communication Association, 2008, pp. 1618-1621.

Král, P., et al., "Dialogue Act Recognition Approaches," Computing and Informatics, vol. 29, 2010, pp. 227-250.

Kumar, N., et al., "Automatic Keyphrase Extraction from Scientific Documents Using N-gram Filtration Technique," Proceedings of the $8^{th}$ ACM symposium on Document engineering, 2008, pp. 199-208.

Mikolov, T., et al., "Efficient Estimation of Word Representations in VectorSpace," Proceedings of the International Conference on Learning Representations (ICLR), arXiv:1301.3781v3, 2013, 12 pages.

Ponte, J.M., et al., "Text Segmentation by Topic," Computer Science Department, University of Massachusetts, Amherst, 1997, 13 pages.

Ramos, J., "Using TF-IDF to Determine Word Relevance in Document Queries," Proceedings of the First Instructional Conference on Machine Learning, 2003, 4 pages.

Rosenfeld, R. "The CMU Statistical Language Modeling Toolkit and its use in the 1994 ARPA CSR Evaluation," Proceedings of the Spoken Language Systems Technology Workshop, 1995, pp. 47-50.

Stolcke, A., "SRILM—An Extensible Language Modeling Toolkit," Seventh International Conference on Spoken Language Processing, 2002, 4 pages.

Stolcke, A., et al., "Automatic Linguistic Segmentation of Conversational Speech," IEEE, vol. 2, 1996, pp. 1005-1008.

Zimmerman, M., et al., "Joint Segmentation and Classification of Dialog Acts in Multiparty Meetings," Acoustics, Speech and Signal Processing, 2006, pp. 581-584.

* cited by examiner

AUTOMATED SYSTEM AND METHOD TO PRIORITIZE LANGUAGE MODEL AND ONTOLOGY EXPANSION AND PRUNING

CROSS REFERENCE TO RELATED APPLICATIONS

This application is a non-provisional patent application claiming priority to Provisional Patent Application Ser. No. 62/748,639, filed Oct. 22, 2018 which is hereby incorporated by this reference in its entirety as if fully set forth herein.

BACKGROUND

Field

Embodiments of the present invention relate to language models and ontologies, and more particularly, to a system and method for automatically prioritize language mode and ontology expansion and pruning.

Background

In speech recognition, a language model (LM) is a graph of probabilities associated to word transitions from a known vocabulary, such as a word lattice. Word embedding is the collective name for a set of language modeling and feature learning techniques in natural language processing (NLP) where words or phrases from the vocabulary are mapped to vectors of real numbers. Some approaches to language model development include term frequency inverse document frequency (TF-IDF) and word similarity. For instance, vocabulary in the insurance domain is expected to differ greatly from vocabulary in the telecommunications domain. To create a LM for use in a specific domain, texts are gathered from various sources such as websites, chat logs, call logs, documentation, and other sources in that domain, but each such domain may use different terms or syntax for the same meaning. There is a need for a system and method to automatically prioritize language model and ontology expansion and pruning.

BRIEF SUMMARY OF THE DISCLOSURE

Accordingly, the present invention is directed to a system and method for a system and method for automatically prioritize language mode and ontology expansion and pruning that obviates one or more of the problems due to limitations and disadvantages of the related art.

In accordance with the purpose(s) of this invention, as embodied and broadly described herein, this disclosure, in one aspect, relates to a computer product comprising computer executable code embodied in a non-transitory computer readable medium that, when executing on one or more computing devices performs a method of normalizing terminology and phrases within a language model for a language domain. The method includes receiving text from a plurality of platforms; determining whether the text includes a term in a stored data model; identifying if a term that does exist in the data model appears in a new context; passing the term in the new context to a human for determination if the term should be added to a training example in the new context for retraining the data model; if the term does not appear in the new context, checking the term for frequency of use in a known context and adding the term in the known context to the training example with a new priority if the frequency has reached a predetermined threshold; and recompiling the language model based on the term in context.

In another aspect, the disclosure relates to a method of adding terms to a language model based on use. The method includes receiving text from a plurality of platforms; determining whether the text includes a term in a stored data model; identifying if a term that does exist in the data model appears in a new context; passing the term in the new context to a human for determination if the term should be added to a training example in the new context for retraining the data model; if the term does not appear in the new context, checking the term for frequency of use in a known context and adding the term in the known context to the training example with a new priority if the frequency has reached a predetermined threshold; and recompiling the language model based on the term in context.

In another aspect, the disclosure relates to a method of removing terms from a language model based on use. The method includes receiving text from a plurality of platforms; determining whether the text includes a term in a stored data model; if the term is in the data model, determining a frequency of use of the term in the text in a context in which the term appears in the data model; deleting the term in context from a training example for the data model if the frequency of use falls below a predetermined threshold; and recompiling the language model based after removing the term in the context from the training example.

Further embodiments, features, and advantages of the system and method for a system and method for automatically prioritize language mode and ontology expansion and pruning, as well as the structure and operation of the various embodiments of the system and method for a system and method for automatically prioritize language mode and ontology expansion and pruning, are described in detail below with reference to the accompanying drawings.

BRIEF DESCRIPTION OF THE DRAWINGS

The accompanying figures, which are incorporated herein and form part of the specification, illustrate the system and method for automatically prioritize language mode and ontology expansion and pruning. Together with the description, the figures further serve to explain the principles of the system and method for automatically prioritize language mode and ontology expansion and pruning described herein and thereby enable a person skilled in the pertinent art to perform and use the system and method for automatically prioritize language mode and ontology expansion and pruning.

DETAILED DESCRIPTION

Reference will now be made in detail to embodiments of the system and method for a system and method for automatically prioritize language mode and ontology expansion and pruning with reference to the accompanying figures. The same reference numbers in different drawings may identify the same or similar elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Figure 1:
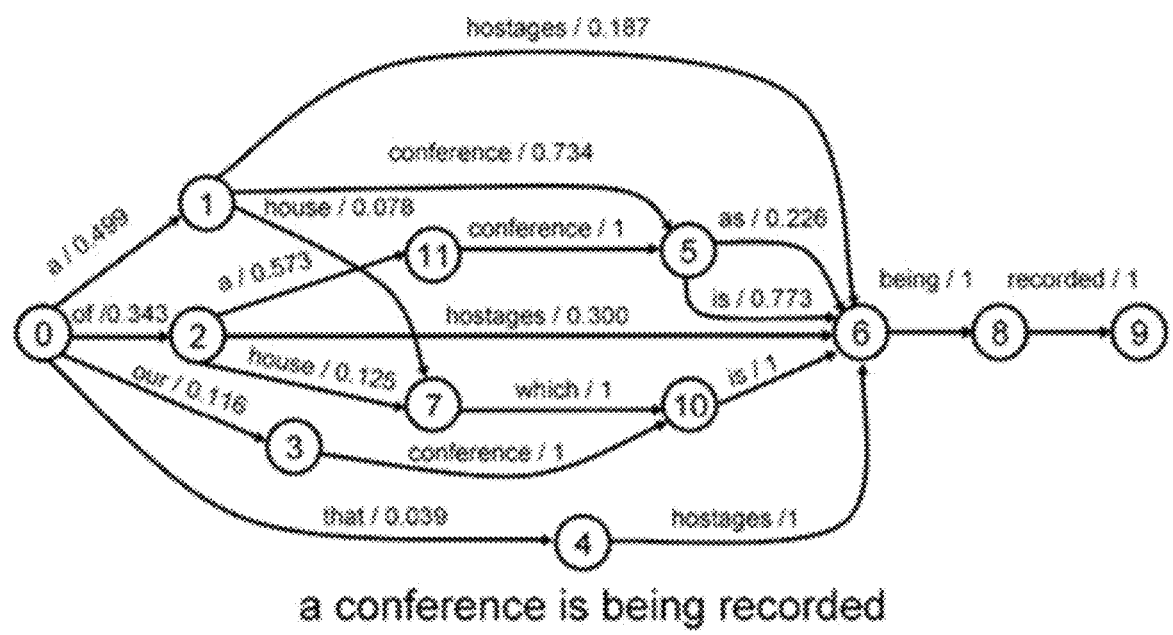
FIG. 1 is an example of a word lattice.

To create a language model (LM) for use in a specific domain, texts are gathered from various sources such as websites, chat logs, call logs, documentation, and other sources in that domain. Once the texts are aggregated, LM construction toolkits such as the CMU [1], SRI[2], or IRST [3] are applied to the data. They extract the vocabulary used within the texts and the statistics of their use with other vocabulary, such as unigrams, bigrams, and trigrams. These statistics can then be used to calculate a priori statistics of sentences that can be formed using the known vocabulary, which are organized in a lattice. A word lattice is an acyclic directed graph with a single starting node and edges labeled with a word and its corresponding probability of following the current word in the source texts. By following a path through the lattice from the starting point to any particular node, the a priori probability of that series of words (i.e. a sentence) appearing in the domain specific texts can be calculated. In the case of FIG. 1, the subject phrase is "a conference is being recorded." An example of algorithms as applied to traverse a word lattice can be found at https://www.slideserve.com/kipling/an-evaluation-of-lattice-scoring-using-a-smoothed-estimate-of-word-accuracy, which is incorporated herein in its entirety as background information.

A different approach to modeling word usage in context is to construct vectors to represent each word in a N-dimensional vector space. These vectors are manipulated during training based on observing where terms occur in the context of the surrounding terms. Terms that occur in the same context are moved closer to alignment. Terms that do not occur in the same context are moved further away. Once trained, the set of vectors can be used to reason about the similarity of words by performing vector arithmetic, such as measuring the distance between two points in the vector space. This approach is known as word embeddings [4], and is a way to group similar terms in a corpus together. Both the LM and word embedding approaches are unsupervised in that they require no human effort to construct. The training algorithms are simply given large training corpora and they use term positions and statistics within the corpora to build a model.

In contrast to models showing the statistical relationship between terms in a training corpora, data modeling approaches seek to define deeper relationships between terms such as hierarchies and negations. For such models there are two common structures used. The simpler form is a taxonomy, which is simply a tree of entities that form a hierarchy. For example, you could create a taxonomy of food where the entities are individual food items such as cheddar cheese, peas, corn, apples, pork, skim milk, etc. You would then create low level classes of foods like red meat, white meat, all cheese, all milk, families of fruits and vegetables, etc. Then you group all of the specific individuals into the classes they belong. Next you create higher level classes such as meat, fish, dairy, fruit, vegetables, etc. and group the classes of foods into the higher level classes. Finally, you can create the top layers of animal products, and non-animal products and put them under the root node of food. In this way you have constructed a taxonomy of food that you can go from specific examples to more and more general classes by following the tree backwards. You can also do simple reasoning like parent-of or sibling-of relationships, and find the least common ancestor between two individuals, like animal products for milk and pork.

For many cases this tree structure is enough to model data and process it. But more complicated relationships, like multiple inheritance and applying logical assertions, require storing data and meta data in a graph form. This is where ontologies come in. An ontology is a directed graph with four primary components: individuals, classes, attributes, and relations. There are many more components possible like events and restrictions as well. Ontologies allow for very rich data modeling with complex relationships and logical inferences about the data. There are many ways to construct ontologies and several different syntaxes for expressing and storing them. Taxonomies and ontologies typically require some human effort to construct. They may be seeded by some statistical observations from corpora, but the relationships between terms are usually defined or refined by humans. These models are concerned with the logical inference that can be drawn from terms within them and therefore require at least some logical relations to be encoded within them by humans.

Figure 2:
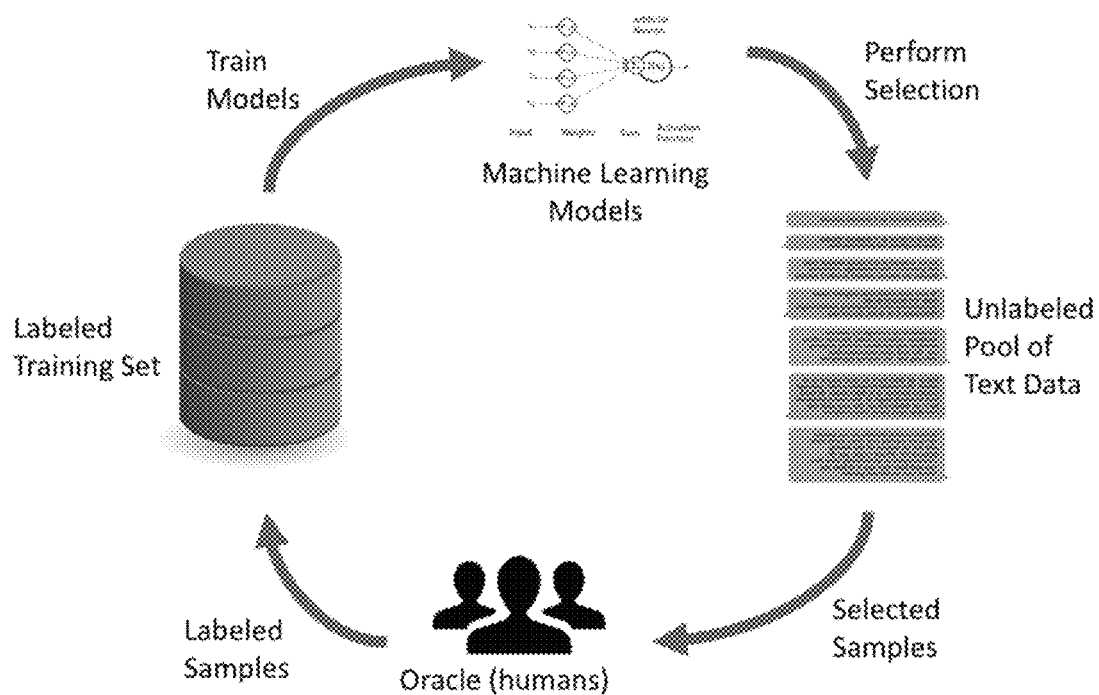
FIG. 2 illustrates an active learning process according to principles described herein.

Human-in-the-loop (HITL) is a subfield of Machine Learning where the model requires some form of human interaction. A common HITL approach is known as Active Learning. With active learning an existing model is supplied with a large pool or stream of unlabeled samples. The model then chooses which samples it thinks would be most informative to know the label for based on a selection strategies, of which there are several commonly used. Human oracles are then shown the selected samples and give them labels. These labeled samples are added to the training data to retrain the model from. In this way the model will learn more quickly from less training data then given a large sample of labeled results that contain many duplicated features. This active learning process is shown in FIG. 2.

Language model and ontology refinement for Intelligent Virtual Assistants (IVAs) is described herein. It is not necessary for the IVA to understand every possible word in order to understand a user's intention in a query. Computational overhead of unbounded LMs and data models will increase understanding latency. However, some words, such as those referring to products or services, are important to understand.

Therefore it is desirable to monitor user communication channels for new terminology that should be understood. Personal communication texts such as emails, instant messaging, and social media are particularly challenging due to their open vocabulary that continuously grows. There are constantly new products, applications, devices, terminology, slang and abbreviations being created and used within such communication channels. In order to deal with the evolving nature of internet language in a timely fashion, automated methods to detect high value words for insertion into LMs and data models are needed. Conversely, words that fall out of use, such as discontinued products or cultural references that are no longer popular, should be removed to maintain the size of models and speed traversals through them.

Herein a system and method to detect and prioritize insertions of new terminology into language and data models. Also provided herein are a system and method to prioritize removal of unused terms from such models to limit their growth and searching latency. In order to discover new terms to add to the IVA's knowledge, several content streams may be monitored. For example, one stream may be trending topics in social media platforms. These may originate from Twitter, Facebook, Pinterest or similar sites where users are actively communicating around topics. As topics gain popularity, they begin to "trend" by rising to the top of the subjects or topics that people are communicating about.

For example, during the holiday season there are new products such as toys and electronic devices that are released to take advantage of the seasonal increase in consumer spending. Suppose one such product is a new smart phone device such as the Google Pixel. When the device is announced or released, there is a sudden emergence in conversations around the topic of the Pixel, where before the term was not related to the electronics domain at all, or may not have even existed if it is an original name. By monitoring trending topics we will observe a sudden appearance of an unknown term, or a term that is not previously associated to the context it appears in.

In a second example, suppose a tropical storm has appeared and is making landfall. Tropical storms are commonly named and if the storm is expected to have a large impact on a populated area many news sites and, therefore, social media sites will experience a sudden spike in conversations around this new name. For IVAs in the travel domain, it will be helpful that these events are understood quickly as many travelers will begin to ask about disruptions caused by the storm.

Additional content streams can be customer e-mail and live chat transcripts, or any other form of customer to company communication channels. For weather occurrences, feeds such as the NOAA and Weather Channel can be monitored. News sites and aggregates of new feeds can also be ingested. From these sources without the construct of trends, terms can be counted over a sliding time window such as a day or week to create a set of trending terms.

Regardless of the source, when new terminology appears in trends we first consult the existing LM and data models used by the IVA. If the term is unknown to the LM it must be prioritized for addition. This prioritization can be based on any predetermined characteristic, e.g., frequency, topic, or source. For example, a frequency chart of mentions across multiple channels/source may be populated to determine the prevalence of the new term. For example, if a new term is only trending within a specific source such as Twitter, it may refer to some isolated phenomenon that may not be as important to be known by the IVA.

On the other hand, a new term may be important for the IVA to know to facilitate handling of incoming customer communication. An example of such phenomenon was the volcanic events that occurred in Iceland in 2010, which caused an ash cloud that grounded air transportation in Europe and caused a spike in the usage of terms such as "ash" and "volcano" that were previously very low ranked in IVAs for airlines. In the case of a tropical storm name or highly anticipated new product, the term might have been previously heard by the IVA (such as tropical storm name "Michael"), the term should be temporarily highly ranked across multiple sources, i.e., much higher and in a different way than the given name "Michael" might previously have been encountered in the existing ontology. That is, the context for an existing term has changed.

We can use this coverage of trending terms across multiple sources, e.g. external to the IVA or in conjunction with the IVA, to inform the usage of terms and to prioritize their addition to or usage in the data model/language model. For example, the frequency with which a term appears, context, and/or threshold counts can factor in the prioritization/ addition of a term. In one aspect, a human could provide input for retraining the model based on new terms, including recommending a new term's priority and how that term should be deployed to the IVA. In the inverse, a term could be removed or priority reduced based on these factors, for example, when the volcano eruption is no longer a factor in air travel or the hurricane has passed, as discussed further below.

Figure 3:
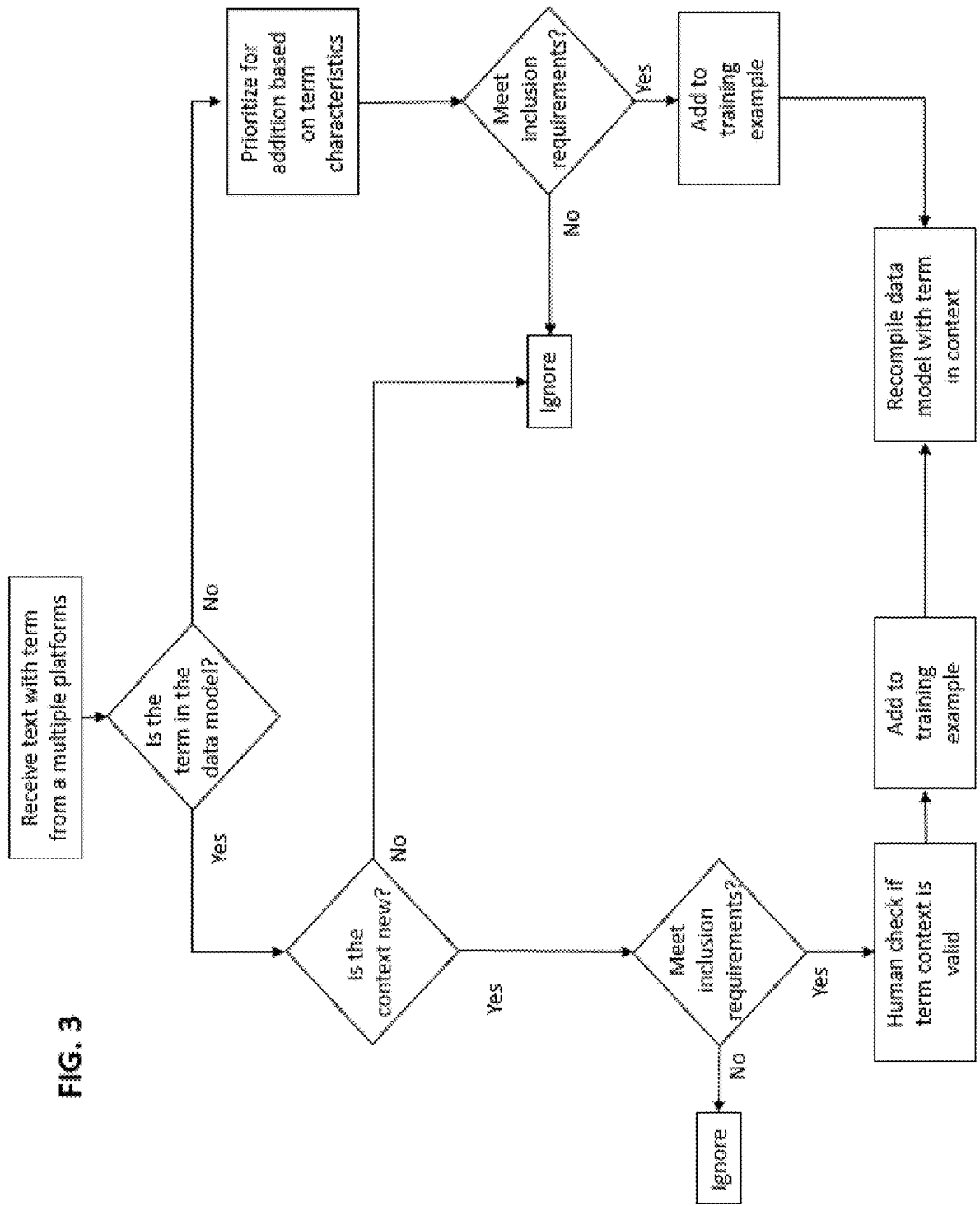
FIG. 3 is a flowchart showing an example set of steps for performing a method as described herein.

In some cases the term will be known, but the context it appears in is new. In the above Google Pixel example, the word "pixel" may already appear in the IVA's vocabulary, but in its ontology it is used for display or camera resolution. To detect usage, we can create embedding models from sliding windows of time using the text from the various input sources. If the existing term becomes embedded along with words that were not previously associated with the term, such as "iPhone", "Apple", or "Google" in the case of the Pixel, we can determine that the new usage of the existing term indicates a new object. In these cases the ontology or other data models will need to be updated to reflect the alternative usage and this update will be prioritized the same way as a new term. Once terms cross a predefined threshold, which is adjustable based on the availability of human annotators, they are given to a human along with example context to be added to the data models and/or LMs. This process of the model selecting its own training data is a special case of HITL known as Active Learning [5]. The human will then add the term to the ontology or update the ontology to reflect the new usage of the existing term. For new terms they will need to be added to the LMs as well so that speech recognition engines will be able to decode the word successfully. A flow chart for an exemplary implementation is provided in FIG. 3.

For an IVA, how a new term is being embedded can be studied. For example, if we look at previous versions of a word lattice or word embedding model, new text can be fed into the model to see how existing terms are being embedded with respect to new pairs or strings of terms. New usage of a term can therefore be identified and its new meaning/usage incorporated into the ontology/language model. This allows for the new usage to be disambiguated based on context. For example, the term can be updated in the ontology and its meaning updated. Its appearance in the language model/ word lattice or word embedding model can therefore be changed to reflect the updated usage.

While monitoring streams of trending topics and terminology from various sources, a list of known vocabulary is maintained. This list reflects all terms known to the IVA through the LMs and data models. Each term in the vocabulary is associated to a timestamp of last mention. When a term is encountered in the input streams and it exists in the vocabulary, the timestamp associated to the term is updated. If a product is discontinued or a tropical storm passes over, we would expect the usage of such terms will diminish over time. Once a term has not been mentioned longer than some tunable cutoff period, over one year for example, it will be deleted from the LMs and data models of the IVA causing the IVA to "forget" the unused term. In this way terms that have a lifespan are not maintained in the LMs and data models, which will prevent unbounded growth and steadily increasing time to search and traverse the models. As the pruning requires no human intervention it can be done automatically, however human review can be used if desired to approve the modifications.

According to principles described herein, the time from when a new term enters use and its adoption by an IVA (or other language based system) can be reduced, thus causing an improvement in the functioning such a device.

According to principle described herein, a human may be involved in determining thresholds by which the system may then run automatically for addition of trending terms and removal of decreasing terms. In the case of addition, a human in the loop may improve retraining based on new terms because a human can provide context for use in retraining the model and recommend priority. Such human activity in conjunction with the automated system of language model and word embeddings described above, can increase the speed with by which the automated models can be retrained to account for trending and declining terms.

Throughout this application, various publications may have been referenced. The disclosures of these publications in their entireties are hereby incorporated by reference into this application in order to more fully describe the state of the art to which this invention pertains:

[1] Ronald Rosenfeld. The cmu statistical language modeling toolkit and its use in the 1994 arpa csr evaluation. In Proceedings of the Spoken Language Systems Technology Workshop, pages 47{50, 1995.

[2] Andreas Stolcke. Srilm-an extensible language modeling toolkit. In Seventh international conference on spoken language processing, 2002.

[3] Marcello Federico, Nicola Bertoldi, and Mauro Cettolo. Irstlm: an open source toolkit for handling large scale language models. In Ninth Annual Conference of the International Speech Communication Association, 2008.

[4] Tomas Mikolov, Kai Chen, Greg Corrado, and Jeffrey Dean. Efficient estimation of word representations in vector space. arXiv preprint arXiv:1301.3781, 2013.

[5] Burr Settles. Active learning. Synthesis Lectures on Artificial Intelligence and Machine Learning, 6(1):1{114, 2012.

https://www.slideserve.com/kipling/an-evaluation-of-lattice-scoring-using-a-smoothed-estimate-of-word-accuracy.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A computer program product for automatically updating a language model for an intelligent virtual assistant (IVA) comprising computer executable instructions embodied in a non-transitory computer readable medium that, when executed by one or more processors, cause the one or more processors to:

ingest language data from internet-based content streams comprising social media, domain-specific communications channels, live chat transcripts, emails, news websites, wherein the internet based content streams are specific to a domain of an IVA;

process the language data using a language model toolkit running on a processor to extract vocabulary from the ingested language data, the extracted vocabulary comprising terms;

count the terms over a sliding window to create a set of trending terms;

apply a word embedding model to determine usage of select ones of the trending terms in context;

compare the select ones of trending terms to terms stored in a language data model specific to the IVA to determine if the trending terms have a match in the stored terms;

upon determination that one of select ones of the trending terms is included in the language data model, identify a context for the one of the select ones of the trending terms as a known context or a new context;

upon determination that the context is a new context, pass the one of the select ones of the trending terms in the new context to a human for determination whether the one of the select ones of the trending terms should be added to a language training example for the IVA in the new context for retraining the language data model;

upon determination that the one of the select ones of the trending terms does appear in the known context, check the one of the select ones of the trending terms for frequency of use in the known context in the ingested language data and add the one of the select ones of the trending terms in the known context to the training example with a new priority upon determining that the frequency has reached a predetermined threshold;

recompile the language model based on the one of the select ones of the trending terms in the known context or the new context; and adopt the recompiled language model into the IVA.

2. The computer program product of claim 1, further comprising additional instructions embodied in the non-transitory computer readable medium that, when executed by the one or more processors, cause the one or more processors to, upon determination that the one of the select ones of the trending terms is not in the language data model, determine a frequency of appearance of the one of the select ones of the trending terms in the ingested language data and, when the frequency crosses a predetermined threshold, adding the one of the select ones of the trending terms to the training example as the one of the select ones of the trending terms appears in the known context.

3. The computer program product of claim 1, further comprising additional instructions embodied in the non-transitory computer readable medium that, when executed by the one or more processors, cause the one or more processors to ignore any of the trending terms that do not meet the predetermined threshold.

4. The computer program product of claim 1, further comprising additional instructions embodied in the non-transitory computer readable medium that, when executed by the one or more processors, cause the one or more processors to delete known terms from the language data model upon determination that the frequency of use of the one of the select ones of the trending terms in the known context falls below a predetermined threshold.

5. The computer program product of claim 1, wherein the predetermined threshold is determined automatically based on predetermined values stored in a digital storage device.

6. The computer program product of claim 1, wherein the one of the select ones of the trending terms is passed to a human only when the one of the select ones of the trending terms in the new context meets a predetermined threshold based on parameters of an existing ontology.

7. A computer-implemented method of automatically adding terms to a language model based on use, the method comprising:

ingesting language data from internet-based content streams comprising social media, domain-specific communications channels, live chat transcripts, emails, news websites, wherein the internet based content streams are specific to a domain of an IVA;

processing the language data using a language model toolkit running on a processor to extract vocabulary from the ingested language data, the extracted vocabulary comprising terms;

counting the terms over a sliding window to create a set of trending terms;

applying a word embedding model to determine usage of select ones of the trending terms in context;

comparing the select ones of trending terms to terms stored in a language data model specific to the IVA to determine if the trending terms have a match in the stored terms;

upon determination that one of select ones of the trending terms is included in the language data model, identifying a context for the one of the select ones of the trending terms as a known context or a new context;

upon determination that the context is a new context, passing the one of the select ones of the trending terms in the new context to a human for determination whether the one of the select ones of the trending terms should be added to a language training example for the IVA in the new context for retraining the language data model;

upon determination that the one of the select ones of the trending terms does appear in the known context, checking the one of the select ones of the trending terms for frequency of use in the known context in the ingested language data and add the one of the select ones of the trending terms in the known context to the training example with a new priority upon determining that the frequency has reached a predetermined threshold;

recompiling the language model based on the one of the select ones of the trending terms in the known context or the new context; and adopting the recompiled language model into the IVA.

8. The method of claim 7, further comprising, upon determining that the one of the select ones of the trending terms is not in the language data model, determining a frequency of appearance of the one of the select ones of the trending terms in the ingested language data and, when the frequency crosses a predetermined threshold, adding the one of the select ones of the trending terms to the training example as the one of the select ones of the trending terms appears in the known context.

9. The method of claim 7, further comprising ignoring trending terms that do not meet the predetermined threshold.

10. The method of claim 7, further comprising deleting known terms from the language data model upon determining that the frequency of use of the one of the select ones of the trending terms in the known context falls below a predetermined threshold.

11. The method of claim 7, wherein the predetermined threshold for adding a term to the training model is met is determined automatically based on predetermined values stored in a digital storage device.

12. The method of claim 7, wherein the one of the select ones of the trending terms is passed to a human only when the one of the select ones of the trending terms in the new context meets a predetermined threshold based on parameters of an existing ontology.

13. A computer-implemented method of automatically removing terms from a language model based on use, the method comprising:

ingesting language data from internet-based content streams comprising social media, domain-specific communications channels, live chat transcripts, emails, news websites, wherein the internet based content streams are specific to a domain of a IVA;

processing the language data using a language model toolkit running on a processor to extract vocabulary from the ingested language data, the extracted vocabulary comprising terms;

counting the terms over a sliding window;

comparing the terms to terms stored in a language data model specific to the IVA to determine if the terms have a match in the stored terms;

upon determination that a term is included in the language data model, determining a frequency of use of the term in the ingested language data in a context in which the term appears in the language data model;

automatically deleting the term in context from a training example for the language data model without further human intervention upon determining that the frequency of use falls below a predetermined threshold;

recompiling the language model based after deleting the term in the context from the training example; and adopting the recompiled language model into the IVA.

14. A system for selecting actions to perform for an entity based on content items comprising:

at least one processor; and a memory storing instructions that, when executed by the at least one processor, cause the at least one processor to:

ingest language data from internet-based content streams comprising social media, domain-specific communications channels, live chat transcripts, emails, news websites, wherein the internet based content streams are specific to a domain of an IVA;

process the language data using a language model toolkit running on a processor to extract vocabulary from the ingested language data, the extracted vocabulary comprising terms;

count the terms over a sliding window to create a set of trending terms;

apply a word embedding model to determine usage of select ones of the trending terms in context;

compare the select ones of trending terms to terms stored in a language data model specific to the IVA to determine if the trending terms have a match in the stored terms;

upon determination that one of select ones of the trending terms is included in the language data model, identify a context for the one of the select ones of the trending terms as a known context or a new context;

upon determination that the context is a new context, pass the one of the select ones of the trending terms in the new context to a human for determination whether the one of the select ones of the trending terms should be added to a language training example for the IVA in the new context for retraining the language data model;

upon determination that the one of the select ones of the trending terms does appear in the known context, check the one of the select ones of the trending terms for frequency of use in the known context in the ingested language data and add the one of the select ones of the trending terms in the known context to the training example with a new priority upon determining that the frequency has reached a predetermined threshold;

recompile the language model based on the one of the select ones of the trending terms in the known context or the new context; and adopt the recompiled language model into the IVA.

15. The system of claim 14, wherein the instructions, when executed by the one or more processors, cause the one or more processors to, upon determination that the one of the select ones of the trending terms is not in the language data model, determine a frequency of appearance of the one of the select ones of the trending terms in the ingested language data and, when the frequency crosses a predetermined threshold, adding the one of the select ones of the trending terms to the training example as the one of the select ones of the trending terms appears in the known context.

16. The system of claim 14, wherein the instructions, when executed by the one or more processors, cause the one or more processors to ignore any of the trending terms that do not meet the predetermined threshold.

17. The system of claim 14 wherein the instructions, when executed by the one or more processors, cause the one or more processors to delete known terms from the language data model upon determination that the frequency of use of the one of the select ones of the trending terms in the known context falls below a predetermined threshold.

18. The system of claim 14, wherein the predetermined threshold is determined automatically based on predetermined values stored in a digital storage device.

19. The system of claim 14, wherein the one of the select ones of the trending terms is passed to a human only when the one of the select ones of the trending terms in the new context meets a predetermined threshold based on parameters of an existing ontology.

* * * * *